United States Patent [19]

Somers

[11] Patent Number: 4,512,996
[45] Date of Patent: Apr. 23, 1985

[54] BENZOYLECGONINE OR BENZOYLNORECGONINE AS ACTIVE AGENTS FOR THE TREATMENT OF RHEUMATOID ARTHRITIS

[76] Inventor: Lowell Somers, 16630 Mountain View Rd., Desert Hot Springs, Calif. 92240

[21] Appl. No.: 584,830

[22] Filed: Feb. 29, 1984

Related U.S. Application Data

[60] Division of Ser. No. 448,928, Dec. 13, 1982, Pat. No. 4,469,700, which is a continuation of Ser. No. 275,307, Jun. 19, 1981, abandoned.

[51] Int. Cl.$^3$ .............................................. A61K 31/46
[52] U.S. Cl. ..................................... 514/304; 514/825
[58] Field of Search .............................. 424/262, 265

[56] References Cited

PUBLICATIONS

S. J. Mule et al., Life Sciences, 19, pp. 1585–1596 (1976).
Misra et al., Research Comm. in Chemical Pathology & Pharmacology, 13, pp. 579–584 (1976), +11, pp. 663–666 (1975).
Misra et al., J. Pharm. Pharmoc. 27, pp. 784–786 (1975).
Ann. Rev. Pharmacol. Toxical., 1979, 19:469–490, CA 83 172831b.
Research Communications in Chemical Pathology and Pharmacology, vol. 11, No. 4, Aug. 1975.
Medical World News, *Long-Shot Hyperbaric Therapy Sets New Record*, pp. 19–20, Oct. 15, 1979.
Arthritis News Today, *Esterene in the Treatment of Rheumatoid Arthritis*, vol. 2, No. 7, Apr. 1980.

*Primary Examiner*—Stanley J. Friedman
*Attorney, Agent, or Firm*—Klein, Szekers & Fischer

[57] ABSTRACT

Pharmaceutical formulation containing benzoylecgonine and/or benzoylnorecgonine and their use in the treatment of rheumatoid arthritis are disclosed.

6 Claims, No Drawings

BENZOYLECGONINE OR BENZOYLNORECGONINE AS ACTIVE AGENTS FOR THE TREATMENT OF RHEUMATOID ARTHRITIS

CROSS REFERENCE TO RELATED APPLICATIONS

This application is a divisional of presently pending application Ser. No. 448,928, filed on Dec. 13, 1982, now U.S. Pat. No. 4,469,700, which is a continuation of application Ser. No. 275,307, filed on June 19, 1981, now abandoned.

BACKGROUND OF THE INVENTION

1. Field of the Invention

This invention relates to pharmaceutical compositions and dosage forms and their use in the treatment of chronic disease. More particularly, it concerns pharmaceutical compositions and dosage forms and their use in the treatment of the pain and locomotor dysfunction of rheumatoid arthritis.

2. Discussion of Prior Art

Rheumatoid arthritis is a serious, often crippling, disease characterized by pain and locomotor dysfunction. As pointed out by Nickander et al in their article "Nonsteroidal Antiinflammatory Agents" which appeared at *Ann. Rev. Pharmacol. Toxical.*, 1979, 19:469-90, this sort of pain and locomotor dysfunction are among man's most common and frustrating afflictions. The gravity of this disease has led to the investigation and/or adoption of a wide range of drugs for its alleviation. Aspirin has been commonly used since the turn of this century. Other major drugs for arthritis have historically included indomethacin, other salicylates, phenylbutazone, steroids and gold. While more recently, fenoprofen, ibuprofen, naproxen, sulindac and tolmetin have been approved for use in the United States.

While these compounds can offer antiinflammatory, antipyretic and analgesic effects and have proven helpful in the management of rheumatoid arthritis in many patients, when combined with other modalities such as proper rest, exercise, physical therapy and surgery, they are less than ideal. Many exhibit serious side-effects with many patients, particularly gastrointestinal damage and renal toxicity. Each of these materials have the failing of being far from universal—some patients will respond to one material while others respond favorably only to others.

Cocaine and cocaine free base have been employed in the management of rheumatoid arthritis for a number of years. I have demonstrated, through clinical experiments on a range of patients suffering from rheumatoid arthritis, the effectiveness of this treatment.

Unfortunately for this possible therapeutic use, cocaine and cocaine free base are widely regarded as materials of abuse. It is most unlikely that the regulatory and drug enforcement agency issues will ever be resolved to a point that cocaine or its free base can be available on as widespread a basis as would be required for their use in the treatment of sufferers of rheumatoid arthritis. In addition, certain individuals can develop dependence upon these materials and/or exhibit symptoms of intoxication when using them.

What is needed is a pharmaceutical preparation and/or dosage form and a method for its use that does not involve cocaine or its free base, that does not present the untoward physiological effects of cocaine but which acts therapeutically in the manner of cocaine to alleviate the pain and motor dysfunction of rheumatoid arthritis.

STATEMENT OF THE INVENTION

It has now been found that benzoylecgonine and its related compound benzoylnorecgonine are therapeutically effective for alleviation of the pain of rheumatoid arthritis and restoration of motor dysfunction of rheumatoid arthritis in humans and other mannals. The compounds are preferably administered in carriers as pharmaceutically acceptable formulations.

DETAILED DESCRIPTION OF THE INVENTION

Benzoylecgonine and benzoylnorecgonine are the active agents employed herein. Fish and Wilson, in *J. Pharm. Pharmac.* 1969 21 Suppl, 135S-138S. presented results showing formation of benzoylecgonine

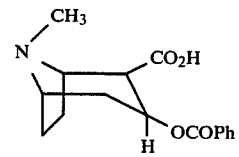

by mammals as a metabolite of cocaine. Misra et al summarized and reported at Volume 13, No. 4, *Research Communications in Chemical Pathology and Pharmacology* (April, 1976, page 579) the finding of benzoylnorecgonine,

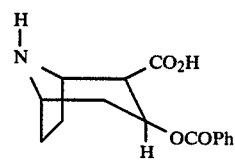

as a mammalian cocaine metabolite, as well.

Routes for the compounds' synthesis have been published. Schmidt and Werner disclose in *Ann.* 653, 184-94 (1962) the conversion of benzoylecgonine (I) to benzoylnorecgonine (II) by, for example, putting 1.16 g of I in 250 cc $H_2O$, adding, over 30 minutes, 48 cc of 3% $KMnO_4$ and stirring for 5 hours at a pH held below 8 by gradual $H_2SO_4$ addition and thereafter filtering and recovering (II) by freeze drying and repeated recrystallization from ethanol. Findlay in *J. Amer. Chem. Soc.* 82 (1960) 4642-4644 discloses that benzoylecgonine can be formed by refluxing cocaine in water for 10 hours and then cooling to recover the benzoylecgonine by crystallization.

Method of Administration

Administration of a therapeutically effective dose of the active compounds to a human or other warm-blooded patient afflicted with rheumatoid arthritis can be via appropriate pharmaceutical formulation and any of the accepted modes for repeated administration of agents for the treatment of inflammation or pain and the prophylaxis thereof. Thus, administration can be for example orally, rectally, bucally, nasally, vaginally topically (for transdermal delivery) or via inhalation. The formulations suitable for such modes of administration include solid, semisolid and liquid formulations which can include tablets, pills, capsules, powders, solutions, suspensions, creams, lotions, ointments or the like, preferably in unit dosage forms suitable for simple administration of precise dosages.

Oral administration is effected using a convenient daily dosage regimen, such as from 3 to 8 doses per day, preferably 4–6 doses per day, which can be adjusted according to the degree of affliction. Generally, a daily dose of from 1.5 to about 15 mg of the active benzoylecgonine and/or benyoylnorecgonine per kilogram of body weight is used. Most conditions respond to treatment comprising a dosage level of the order of 2.5 to 10 mg. per kilogram of body weight per day. In such an oral mode of administration, a pharmaceutically acceptable nontoxic composition is formed by the incorporation of any of the normally employed excipients, such as, for example, pharmaceutical grades of mannitol, lactose, starch, magnesium stearate, talcum, cellulose, glucose, gelatin, sucrose, magnesium carbonate, and the like. Of course, if desired, other pharmacologically active materials can be incorporated into such formulations to give a combination product.

Transdermal delivery of the benzoylecgonine and/or benzoylnorecgonine compounds, effected by topical administration of a solution, suspension, cream, lotion or similar formulation to the skin of the patient is also effective. Formulations for such use include a carrier which should be a liquid or semisolid that is inert to the active compound and not irritating to the skin. Suitable carriers for solutions include water, aqueous mixed solvents, lower alkanols and alkandiols, for example, ethanol, methanol, isopropanol, ethylene glycol, glycerine, propylene glycol and the like. Suitable bases for salves and creams include pharmaceutically acceptable oils and cream bases and gells. In addition, topical formulations can contain nontoxic auxilary substances such as wetting or emulsifying agents, pH buffering agents and the like. In general, it is preferred to use formulations in which the active compounds are soluble, preferably at least to an extent of about 1% by weight.

In the transdermal (topical) mode of administration, typically from 50 to 500 square centimeters of skin surface is contacted with a 1 to 10% by weight solution or cream of the active compound at least once a day and preferably from three to eight times per day, and preferably four to six times per day, the exact dosage depending upon the degree of affliction. The formulations employed in the transdermal mode of application can, if desired, contain materials to promote transdermal transport. The aforesaid alkanols and alkandiols for example, may promote such transport as many DMSO, surfactants, and the like. In addition, other materials may be added to minimize skin irritation or to treat other conditions or side reactions.

A third mode of administration that is useful is via the mucous membranes of the oral and nasal cavities. This method of administration can be effected using buccal patches or the like for sublingual administration or by inhaling the active benzoylecgonine or benzoylnorecgonine compound as a finely divided power or atomized solution. With inhalation therapy, the benzoylecgonine compound can be delivered to the nasal membranes and to the lungs as a solid powder or as a solution. In either method, the patient can supply the driving force by inhaling or an external force can be used such as a pump, a propellant gas or liquid, or the like. In this mode of therapy, a daily dosage regimen of at least one dose per day is followed, with three to eight doses per day being preferred. Generally, the amount of active benzoylecgonine compound delivered per day is at least 0.5 mg. per kilogram of body weight. Preferably, the amount of benzoylecgonine compound administered per day by inhalation is from 1 to about 8 mg. per kilogram of body weight.

In addition, the benzoylecgonine or benzogylnorecgonine active compound can be administered via vaginal or uteral routes wherein the active compound in a suitable liquid or ointment carrier is applied to the vaginal or uteral membranes. This method of administration employs similar dosages and dosage regimens described above for buccal or nasal administration.

The invention will be further illustrated by the following EXAMPLES. These are presented to exemplify and make clear the invention and are not to be construed as limiting its scope which is defined solely by the claims.

EXAMPLE 1

A. Benzoylecgonine and benzoylnorecgonine are prepared from commercial cocaine by the above-described methods of Finlay and Schmidt and Werner, respectively. The two active compounds are formulated with sorbitol as a powder containing 50% active agent, in sterile water as a 4% solution, and in a carboxymethlcellulose jelly at a 2% concentration.

The active compounds could also, if desired, be presented in association with other pharmaceutically acceptable carriers in pharmaceutical formulations suitable for transdermal, inhalation, nasal, oral or rectal administration. Suitable carriers include solids such as lactose, starch (pharmaceutical grade), dicalcium phosphate, calcium sulfate, kaolin, mannitol and powdered sugar and liquids such as sterile saline or the like.

The formulations for oral, rectal or vaginal administration are advantageously presented in discrete unit dosage forms, such as tablets, capsules, cachets, suppositories, each containing a predetermined amount of the compound, but may also be presented as a powder, or as granules. They may as well be presented as a solution or suspension in an aqueous or non-aqueous liquid such as would be useful for administration. The formulations may be made by any of the known methods and may include one or more of the following accessory ingredients: buffers, flavoring, binding, dispersing, surface-active, thickening, lubricating and coating materials, preservatives, bacteriostats, antioxidants, suppository and ointment bases, coloring agents, and any other acceptable excipients. Unit dosage forms may typically contain from about 0.01 to about 0.1 gram of active compound.

Any skilled artisan can prepare these dosage forms by simply referring to the oral dosage form preparatory procedure outline in "Remington's Pharmaceutical Sciences," Fourteenth Edition (1970), pages 1624 through 1698 inclusive, and the rectal dosage form preparatory procedure outline in the same text at pages 1617 through 1624, inclusive.

B. A group of patients afflicted with rheumatoid arthritis is assembled. They are in pain and have pronounced motor dysfunction as results of their disease. A control group is taken from this group and left untreated. The members of the control group show no improvement during the test. A first test group is selected at random from the patient group. Each member of this first test group rubs 2-4 g quantities of the jelly (40–80 mg of the active caine compound) on their skin three times a day. A second test group takes by inhalation 100 mg. doses of the powder six times a day. A third test group rubs 1–2 ml quantities of the 4% solution on their skin and allows it to evaporate to dryness. This is carried out six times a day. A fourth test group takes orally six times a day capsules made up to contain 80 mg. of the active compound. The patients in each of the four test groups report a reduction of their pain and an improvement in mobility and motor function during the period that the treatment is being administered to them. They report no adverse effects of their treatment.

EXAMPLE 2

The active compounds are individually formulated into 5% by weight ointments in a water-miscible ointment vehicle consisting of polyethylene glycols and propylene glycol.

When 1 g of either of these ointments is rubbed into the skin of test patients suffering from rheumatoid arthritis in a treatment program of six doses per day or 300 mg of active compound per day the patients report improvement in mobility and a decrease in the pain that they normally associate with their arthritic condition.

A series of buccal patches is prepared each incorporating 0.5 g of this ointment. When four to six of these patches are serially placed on the mucous membrane under the tongue they administer the compound throughout the day. Test subjects afflicted with rheumatoid arthritis report a decrease in pain and an increase in mobility when they are receiving this treatment.

What is claimed is:

1. A pharmaceutical formulation for the treatment of rheumatoid arthritis comprising one or more active agents selected from benzoylecgonine and benzoylnorecgonine in amounts of approximately 0.187 mg to about approximately 5.0 mg per dose, per kilogram body weight of the patient, said amounts being effective for treating rheumatoid arthritis in association with a pharmaceutical carrier, the formulation being adapted for oral administration and being an aqueous solution of the active ingredient and comprising one or more pharmaceutical carriers selected from a group consisting of mannitol, lactose, starch, magnesium stearate, talcum, cellulose, glucose, sucrose, gelatin, sorbitol and magnesium carbonate.

2. The formulation of claim 1 and further comprising carboxymethylcellulose jelly.

3. A pharmaceutical formulation for the treatment of rheumatoid arthritis comprising one or more active agents selected from benzoylecgonine and benzoylnorecgonine in amounts of approximately 0.125 mg to about approximately 2.67 mg per dose, per kilogram body weight of the patient, said amounts being effective for treating rheumatoid arthritis in association with a pharmaceutical carrier, the formulation being in a unit dosage form adapted for administration by inhalation or through mucosal membranes of a patient's body.

4. A pharmaceutical formulation for the treatment of rheumatoid arthritis comprising one or more active agents selected from benzoylecgonine and benzoylnorecgonine in amounts effective for treating rheumatoid arthritis in association with a pharmaceutical carrier, the formulation being a water miscible ointment comprising a pharmaceutically acceptable water miscible polyol.

5. The formulation of claim 4 wherein the polyol is selected from a group consisting of polyethylene glycol and propylene glycol.

6. The formulation of claim 4 comprising approximately 50 mg of active ingredient per dose.

* * * * *